United States Patent [19]

Gibson

[11] 4,264,730

[45] Apr. 28, 1981

[54] MEDIUM FOR DETERMINING SENSITIVITY OF KLEBSIELLA AND ENTEROBACTER ORGANISMS TO SELECTED ANTIBIOTICS

[75] Inventor: Sandra F. Gibson, St. Louis, Mo.

[73] Assignee: McDonnell Douglas Corporation, St. Louis, Mo.

[21] Appl. No.: 70,176

[22] Filed: Aug. 27, 1979

Related U.S. Application Data

[63] Continuation-in-part of Ser. No. 829,932, Sep. 1, 1977, abandoned.

[51] Int. Cl.³ .......................... C12Q 1/18; C12Q 1/04
[52] U.S. Cl. ...................................... 435/32; 435/34; 435/38; 435/253

[58] Field of Search ....................... 435/32, 33, 34, 38, 435/253, 822

[56] References Cited

U.S. PATENT DOCUMENTS

| 3,957,583 | 5/1976 | Gibson et al. | 435/33 |
| 4,072,571 | 2/1978 | Gibson et al. | 435/822 X |

Primary Examiner—David M. Naff
Attorney, Agent, or Firm—Gravely, Lieder & Woodruff

[57] ABSTRACT

The sensitivity of Klebsiella and Enterobacter organisms to preselected antibiotics is determined with a medium consisting essentially of a nutrient source for Klebsiella and Enterobacter organisms, about 0.01 to about 0.03 g/l 2,4 dinitro phenyl hydrazone of α-Ketoglutaric acid, about 3.5 to about 6 g/l sodium desoxycholate and the preselected antibiotic.

15 Claims, No Drawings

MEDIUM FOR DETERMINING SENSITIVITY OF KLEBSIELLA AND ENTEROBACTER ORGANISMS TO SELECTED ANTIBIOTICS

REFERENCE TO OTHER APPLICATIONS

This application is a continuation-in-part of application Ser. No. 829,932, filed Sept. 1, 1977, now abandoned, and contains subject matter in common with U.S. Pat. No. 3,957,583 dated May 18, 1976, entitled APPARATUS AND PROCESS FOR DETERMINING THE SUSCEPTIBILITY OF MICROORGANISMS TO ANTIBIOTICS and copending applications Ser. No. 682,659, filed May 6, 1976, entitled KLEBSIELLA AND PNEUMONIAE AND ENTEROBACTER BROTH now U.S. Pat. No. 4,072,571 issued Feb. 7, 1978 and Ser. No. 682,664, filed May 5, 1976, by Charles et al, entitled AUTOMATED MICROBIAL ANALYZER now U.S. Pat. No. 4,118,280 issued Oct. 3, 1978.

BACKGROUND OF THE INVENTION

Gibson et al, U.S. Pat. No. 3,957,583, discloses a process and apparatus for conducting antibiotic susceptibility tests in a relatively short time. In U.S. Pat. No. 3,957,583, the clinical specimen is examined directly without isolating the suspected microorganisms. The basic process of U.S. Pat. No. 3,957,583 involves introducing a specimen into blends of a selective culture medium and known antimicrobial agents. If the specimen contains a microorganism which is favored by the culture medium of the blend, and the microorganism is not susceptible to the antibiotic, the optical characteristics of the blend will change.

It is an object of the present invention to provide a culture medium in which the sensitivity and resistance to known antibiotics of Klebsiella and Enterobacter microorganisms is demonstrated with a high degree of precision.

The major problem encountered with conventional microbial sensitivity tests is the length of time that passes from obtaining a clinical specimen from the patient to selection of a suitable antimicrobial agent that can be expected to control any microorganisms detected. Application Ser. No. 682,659 (now U.S. Pat. No. 4,072,571 issued Feb. 7, 1978) discloses a medium for detecting Klebsiella/Enterobacter microorganisms for a given set of antibiotics.

Also the medium of U.S. Pat. No. 4,072,571 contains ingredients which are detrimental to certain antibiotics. Thus, the medium of the present invention is designed not only to facilitate growth of Klebsiella and Enterobacter but also to retain and enhance the effectiveness of antibiotics, so that one can get an accurate reading of the potency of a particular antibiotic against the Klebsiella and Enterobacter organisms.

Accordingly, it is an object of the present invention to provide a medium which, when used with the apparatus described in U.S. Pat. No. 3,957,583, will allow a clinician to determine within a relatively short period of time (from about 8 to about 12 hours) which of a series of antimicrobial agents will be effective in suppressing the activity of infectious microorganisms.

The broth of the present invention will allow the clinician to test several antibiotics simultaneously to determine the Klebsiella and Enterobacter sensitivity of each. The results obtained allow the clinician to select a backup antibiotic, should the primary antibiotic fail to treat the patient's condition.

SUMMARY OF THE INVENTION

This invention involves a medium for determining sensitivity or resistance of Klebsiella and Enterobacter organisms to pre-selected antimicrobial agents. The medium contains carbon and nitrogen nutrient sources, vitamins, inhibitors to inhibit the growth of undesirable organisms, such as *E. Coli* and gram-negative organisms (which may give false positives for Klebsiella and Enterobacter), and an indicator system which shows metabolic activity of Klebsiella and Enterobacter or lack of this activity in the medium. The basic medium also includes a pre-selected antimicrobial agent whose effectiveness against Klebsiella and Enterobacter is measured by the aforesaid indicator which indicates metabolic activity of Klebsiella and Enterobacter. The medium is usable with the mechanism of Ser. No. 682,664. A precipitate forms in the medium if Klebsiella and Enterobacter are not repressed by the antibiotic of the system. This precipitate is detected by the optical scanning mechanism of U.S. Pat. No. 4,118,280 (Ser. No. 682,664).

DETAILED DESCRIPTION

The culture medium of this invention consists essentially of a nutrient source for Klebsiella and Enterobacter which comprises carbon, nitrogen and vitamins, 2, 4, dinitro phenyl hydrazone of $\alpha$-Ketoglutaric acid to inhibit gram positive organisms and gram negative organisms other than Klebsiella and Enterobacter, sodium desoxycholate to indicate the metabolism of Klebsiella and Enterobacter by changing the light transmitting characteristics of the medium, and a preselected antibiotic whose effectiveness is measured by observing the light transmitting characteristics of the medium.

The culture medium of the present invention contains the following nutrients in the amounts indicated:
Gelysate: about 3.5 to about 6.0 gm/l
Cellobiose: about 7.0 to about 12.0 gm/l
i-Inositol: about 7.0 to about 12.0 gm/l
d-Biotin: about 0.1 to about 0.4 gm/l
Yeast Extract: about 0.1 to about 0.4 gm/l Gelysate is a nitrogen source. It is from BBL and is a gelatin hydrolysate made by pancreatic digestion and is low in cystine and tryptophane.

A suitable substitute for Gelysate is any nitrogen source that is free of sugar. Trypticase or another polypeptone having substantially equivalent characteristics as Gelysate may also be used. Peptones containing low amounts of sugar may be used.

As mentioned the purpose of the Gelysate is to provide nitrogen to the organism.

Celloboise and inositol are carbon sources. The purpose of the celloboise and inositol is to provide sugar for the organism, whose sugar fermentation induces the dramatic change in pH which triggers the indicator as will be discussed hereinafter.

Yeast extract is used to supply necessary minerals and vitamins to the medium.

The culture medium of this invention also contains from about 3.5 to about 6.0 gm/l of sodium desoxycholate. The function of the sodium desoxycholate is to form a precipitate in the presence of Klebsiella and Enterobacter so as to change the light transmitting properties of the medium.

The sodium desoxycholate indicator operates by forming a milky white precipitate under acid conditions. This change is observed and recorded by the mechanism described in U.S. Pat. No. 4,118,280 entitled AUTOMATED MICROBIAL ANALYZER. The indicator also acts to inhibit gram-negative organisms.

The present indicator differs from the indicator of Gibson U.S. Pat. No. 4,072,571 in that no sodium salt of ricinoleic acid is present. This was part of the indicator system of Gibson U.S. Pat. No. 4,072,571, but it is detrimental to antibiotics and thus is eliminated from the present broth.

The concentration of sodium desoxycholate is reduced by a factor of 2 in the present invention as compared to the composition of Gibson U.S. Pat. No. 4,072,571.

The broth of this invention has a pH of 7.5 whereas the broth of Gibson U.S. Pat. No. 4,072,571 is more alkaline at pH 8.0. The activity of the indicator system is initiated when the Klebsiella or Enterobacter organisms utilize the sugars in the broth and cause the production of acid which produces a milky white precynate which is observed by the scanning device of U.S. Pat. No. 4,118,280.

The E. Coli inhibitor comprises 2,4 dinitro phenyl hydrazone of α-Ketoglutaric acid. From about 0.01 gm to about 0.03 gm of 2,4 dinitro phenyl hydrazone of α-Ketoglutaric acid is used per liter of the medium. From about 8 ml to about 12 ml of Brilliant Green (0.13% stock solution), preferably 10 ml, are also used per liter of medium.

The concentration 2,4 dinitro phenyl hydrazone of α-Ketoglutaric acid is reduced by a factor of 16 compared to the concentration of this ingredient in the broth of Gibson U.S. Pat. No. 4,072,571.

Another ingredient present in the broth of Gibson U.S. Pat. No. 4,072,571 and eliminated from the composition of the present invention is 3-(α-Acetonylbenzyl)-4-Hydroxy coumarin. This ingredient too has been found to be detrimental to antibiotics and hence cannot be present in a broth used to determine the susceptibility of Klebsiella and Enterobacter to antibiotics.

In addition to the foregoing, an antibiotic is added to the medium of the present invention to determine the sensitivity of Klebsiella and Enterobacter to the particular antibiotic being tested. The following antibiotics in the respective amounts, based on activity, are used in this invention within the ranges specified:
Cephalothin (Sodium): about 10,000 μg to about 17,500 μg/l
Nalidixic Acid: about 12,500 μg to about 20,000 μg/l
Ampicillin Trihydrate: about 3,500 μg to about 5,000 μg/l
Sodium Colistin: about 40,000 μg to about 55,000 μg/l
Nitrofurantoin: about 7,500 μg to about 15,000 μg/l
Tetracycline HCl: about 7,000 μg to about 10,000 μg/l
Gentamicin Sulfate: about 2,500 μg to about 3,250 μg/l
Trimethoprim-Sulfamethoxazole(1:20): about 2,000 μg to about 3,000 μg/l
Carbenicillin: about 17,500 μg to about 25,000 μg/l
Chloramphenicol: about 17,500 μg to about 25,000 μg/l In formulating the composition of the present invention after the antibiotic is added, the medium is filter sterilized and packaged.

EXAMPLE I

To prepare a 2X medium in an amount of 200 ml, Klebsiella and Enterobacter sensitivity broth is prepared by adding 30.0 gm of sodium desoxycholate to 3000 ml of distilled water. The solution is stirred until the sodium desoxycholate is dissolved. The pH of the solution is then adjusted to 7.5 with either 1 N NaOH or 1 N HCl.

The following nutrients are then added in the respective amounts to the foregoing mixture:
Gelysate: 30.0 gm
Celloboise: 60.0 gm
i-Inositol: 60.0 gm
d-Biotin: 1.5 gm
Yeast Extract: 1.5 gm To the foregoing mixture is added 0.15 gm of 2,4 dinitro phenyl hydrazone of α-Ketoglutaric acid. Then 60 ml of a 0.13% stock solution of Brilliant Green are also added to the mixture.

The resulting mixture is stirred slowly until all of the ingredients have dissolved. The pH is then adjusted to 7.5±0.01. The mixture is divided into 200 ml aliquots prior to addition of the antibiotics. The aliquots are then filter sterilized.

By means of a volumetric flask, 200 ml aliquots of the foregoing medium are dispersed into each of 12 beakers. Into each beaker is added a different antibiotic. The following antibiotics in the respective amounts, based on activity, are used per 200 ml of the medium:
Cephalothin (Sodium): 5,600 μg
Nalidixic Acid: 6,000 μg
Ampicillin Trihydrate: 1,680 μg
Sodium Colistin: 20,000 μg
Nitrofurantoin: 4,000 μg
Tetracycline HCl: 3,200 μg
Gentamicin Sulfate: 1,140 μg
Kanamycin Sulfate: 3,200 μg
Trimethoprim-Sulfamethoxazole(1:20): 1,000 μg
Carbenicillin: 8,000 μg
Chloramphenicol: 8,000 μg

What is claimed is:

1. A broth medium for determining sensitivity of Klebsiella and Enterobacter organisms to a preselected antibiotic consisting essentially of:
   A. a nutrient source for Klebsiella and Enterobacter comprising carbon, nitrogen and vitamins in an amount of from about 17.7 to about 30.8 g/l,
   B. about 0.01 to about 0.03 g/l 2,4 dinitro phenyl hydrazone of α-Ketoglutaric acid to inhibit gram-negative organisms other than Klebsiella and Enterobacter and gram-positive organisms,
   C. about 3.5 to about 6 g/l sodium desoxycholate to indicate the metabolism of Klebsiella and Enterobacter by changing the light transmitting characteristics of the medium, and
   D. from about 2000 to about 55000 μg/l of a preselected antibiotic whose effectiveness in inhibiting metabolism of Klebsiella and Enterobacter is measured by observing the light transmitting characteristics of the medium.

2. The medium of claim 1 including about 8 to about 12 ml (0.13% stock solution) Brilliant Green.

3. The medium of claim 1 wherein the antibiotic is selected from the group consisting of Cephalothin (Sodium), Nalidixic Acid, Ampicillin, Sodium Colistin, Nitrofurantoin, Tetracycline HCl, Gentamicin Sulfate, Kanamycin, Trimethoprim-Sulfamethoxazole, Carbincillin, and Chloramphenicol.

4. A broth medium for determining sensitivity of Klebsiella/Enterobacter organisms to a pre-selected antibiotic consisting essentially of from about 3.5 to about 6 g/l sodium desoxycholate,
from about 3.5 to about 6 g/l gelysate,
from about 7 to about 12 g/l cellobiose,
from about 7 to about 12 g/l i-Inositol,
from about 0.1 to about 0.4 g/l d-Biotin,
from about 0.01 to about 0.03 g/l 2,4 dinitro phenyl hydrazone of α-Ketoglutaric acid,
from about 8 to about 12 ml of 0.13% stock solution to Brilliant Green,
and a pre-selected antibiotic at a pH of about 7.5.

5. The medium of claim 4 wherein the pre-selected antibiotic is Sodium Cephalothin, said antibiotic being present in the amount of about 10,000 to about 17,500 μg/l, based on activity.

6. The medium of claim 4 wherein the pre-selected antibiotic is Nalidixic Acid, said antibiotic being present in the amount of about 12,500 to about 20,000 μg/l, based on activity.

7. The medium of claim 4 wherein the pre-selected antibiotic is Ampicillin Trihydrate, said antibiotic being present in the amount of about 3,500 to about 5,000 μg/l, based on activity.

8. The medium of claim 4 wherein the pre-selected antibiotic is Sodium Colistin, said antibiotic being present in the amount of about 40,000 to about 55,000 μg/l, based on activity.

9. The medium of claim 4 wherein the pre-selected antibiotic is Nitrofurantoin, said antibiotic being present in the amount of about 7,500 to about 15,000 μg/l, based on activity.

10. The medium of claim 4 wherein the pre-selected antibiotic is Tetracycline HCl, said antibiotic being present in the amount of about 7,000 to about 10,000 μg/l, based on activity.

11. The medium of claim 4 wherein the pre-selected antibiotic is Gentamicin Sulfate, said antibiotic being present in the amount of about 2,500 to about 3,250 μg/l, based on activity.

12. The medium of claim 4 wherein the pre-selected antibiotic is Kanamycin Sulfate, said antibiotic being present in the amount of 7,000 to about 9,000 μg/l, based on activity.

13. The medium of claim 4 wherein the pre-selected antibiotic is Trimethoprim-Sulfamethoxazole, said antibiotic being present in the amount of about 2,000 to about 3,000 μg/l, based on activity.

14. The medium of claim 4 wherein the pre-selected antibiotic is Carbencillin, said antibiotic being present in the amount of about 17,500 to about 25,000 μg/l, based on activity.

15. The medium of claim 4 wherein the pre-selected antibiotic is Chloramphenicol, said antibiotic being present in the amount of about 17,500 to about 25,000 μg/l, based on activity.

* * * * *